(12) United States Patent
Osanai et al.

(10) Patent No.: US 9,783,581 B2
(45) Date of Patent: Oct. 10, 2017

(54) METHOD FOR PRODUCING PLASTIC RAW MATERIAL FROM BLUE-GREEN ALGAE

(71) Applicant: RIKEN, Wako-shi, Saitama (JP)

(72) Inventors: Takashi Osanai, Wako (JP); Masami Hirai, Wako (JP); Kazuki Saito, Wako (JP); Hiroko Iijima, Wako (JP); Ayuko Kuwahara, Wako (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 15/114,984

(22) PCT Filed: Jan. 29, 2015

(86) PCT No.: PCT/JP2015/052457
§ 371 (c)(1),
(2) Date: Jul. 28, 2016

(87) PCT Pub. No.: WO2015/115520
PCT Pub. Date: Aug. 6, 2015

(65) Prior Publication Data
US 2016/0347796 A1    Dec. 1, 2016

(30) Foreign Application Priority Data

Jan. 30, 2014    (JP) .................................. 2014-015560

(51) Int. Cl.
| | | |
|---|---|---|
| *C12N 1/12* | (2006.01) | |
| *C07K 14/195* | (2006.01) | |
| *C12P 7/46* | (2006.01) | |
| *C12P 7/56* | (2006.01) | |
| *C12P 7/62* | (2006.01) | |
| *C12P 7/42* | (2006.01) | |
| *C12P 7/54* | (2006.01) | |

(52) U.S. Cl.
CPC .............. *C07K 14/195* (2013.01); *C12P 7/42* (2013.01); *C12P 7/46* (2013.01); *C12P 7/54* (2013.01); *C12P 7/56* (2013.01); *C12P 7/625* (2013.01)

(58) Field of Classification Search
CPC .................................................... C07K 14/405
USPC .......................................... 435/257.1, 257.2
See application file for complete search history.

(56) References Cited

U.S. PATENT DOCUMENTS 4,876,331 A    10/1989    Doi

FOREIGN PATENT DOCUMENTS

JP    1-222788    9/1989

OTHER PUBLICATIONS

Osanai, Takashi, et al., "Increased Cyanobacteria Bioplastic Production Via Sigma Factor SigE Overexpression", White Paper, URL, http://www.sbj.or.jp/2012/wp-content/uploads/file/program/topics/topics2012-7.pdf, 2012, vol. 64 No. 90, pp. 16-17 (with English Translation).
Nakahira, Yoichi, et al., "Global Gene Repression by KaiC as a Master Proccess of Prokaryotic Circadian System", PNAS, 2004, vol. 101, No. 3, pp. 881-885.
Miyake Masato, et al., "Production of Plastic from Carbon Dioxide by Cyanobacteria", Nippon Nogeikagaku Kaishi, 1998, vol. 72, No. 4, pp. 528-531 (with English Translation).
Sudesh, Kumar, et al., "Effect of Increased PHA Synthase Activity on Polyhydroxyalkanoates Biosynthesis in *Synechocystis* sp. PCC6803", International Journal of Biological Macromolecules, 2002, vol. 30, pp. 97-104.
Ehira, Shigeki, et al., "NrrA, a Nitrogen-Regulated Response Regulator Protein, Controls Glycogen Catabolism in The Nitrogen-Fixing *Cyanobacterium anabaena* sp. Strain PCC7120", The Journal of Biological Chemistry, vol. 286, No. 44, pp. 38109-38114.
Wang, Jiangxin, et al., "RNA-seq Based Identification and Mutant Validation of Gene Targets Related to Ethanol Resistance in *Cyanobacterial synechocystis* sp. PCC6803", Biotechnology fo Biofuels, 2012, 5:89, pp. 1-18.
International Search Report for International Application No. PCT/JP2015/052457, dated Apr. 21, 2015.

*Primary Examiner* — Tekchand Saidha
(74) *Attorney, Agent, or Firm* — McCarter & English LLP

(57) ABSTRACT

An object of the present invention is to construct a production system that enables efficient production of organic acids using blue-green algae, which are photosynthetic microorganisms, by utilizing carbon dioxide and thereby increasing an amount of organic acids produced. The present invention relates to blue-green algae overexpressing a clock protein gene and a method for producing organic acids by culturing the blue-green algae.

15 Claims, No Drawings

SEQUENCE LISTING

```
<160> NUMBER OF SEQ ID NOS: 28

<210> SEQ ID NO 1
<211> LENGTH: 900
<212> TYPE: DNA
<213> ORGANISM: Synechocystis sp.PCC 6803

<400> SEQUENCE: 1
gtgcagtctc ccctctccct ctgtcttttt gctcccgaac acgttgccca tagactcagg    60
tctattttcc agggcgatcg ccattaccta tcgactttc aagcactaga tgattttgt     120 gcctttctag aagacaaacc tgagcggatt gattgcctgt tagtctatta cgaagctaat    180
tcccttccag tgctgaatcg tctctatgaa caggggcgat tgttgccgat tattttgctc    240
gaacccagtc cttctgccct agccaaaacc accgacgaac accccaccat tgtctatcac    300
aacgctgaaa ttcatctgcc cgaatcccaa tggtcggaac tgcccaccgt cgtagaccgg    360
gcgatcgccc attacctaca ccttggcccc atctgtaccc tccccaacca aacggaaact    420
atccccgccc cgattgtcga tgaatcatcc caaagctttt tactcctaca acaaagaagg    480
ctggctgaca aacttaaaga aagactcggt tacctaggag tgtactacaa acgtaagccc    540
agtcactttt accgcaactt ttccccccag gaaaaacaag aatacctaga agatttaagc    600
tcccaatatc gagagattat tctcagttat tttagtgacg aaggcacagt taatgacctg    660
ttagatcaat ttgttaatca ggctttcttt gccgacctag ccatttctca aatcctggaa    720
attcacatgg aattaatgga tgaattttcc cagcatctaa agctagaagg gcggagcgaa    780
gaagtcctcc tagactatcg tttagtgttg atcgacatcc tcgcccatct ggggggaaatg    840 tatcgccgtt ccatccccg ggaggacatt ccctttgatg tatattatca gacggattaa    900

<210> SEQ ID NO 2
<211> LENGTH: 299
<212> TYPE: PRT
<213> ORGANISM: Synechocystis sp.PCC 6803

<400> SEQUENCE: 2

Met Gln Ser Pro Leu Ser Leu Cys Leu Phe Ala Pro Glu His Val Ala
1               5                   10                  15

His Arg Leu Arg Ser Ile Phe Gln Gly Asp Arg His Tyr Leu Ser Thr
            20                  25                  30

Phe Gln Ala Leu Asp Asp Phe Cys Ala Phe Leu Glu Asp Lys Pro Glu
        35                  40                  45

Arg Ile Asp Cys Leu Leu Val Tyr Tyr Glu Ala Asn Ser Leu Pro Val
    50                  55                  60

Leu Asn Arg Leu Tyr Glu Gln Gly Arg Leu Leu Pro Ile Ile Leu Leu
65                  70                  75                  80

Glu Pro Ser Pro Ser Ala Leu Ala Lys Thr Thr Asp Glu His Pro Thr
                85                  90                  95
```

```
Ile Val Tyr His Asn Ala Glu Ile His Leu Pro Glu Ser Gln Trp Ser
                100                 105                 110

Glu Leu Pro Thr Val Val Asp Arg Ala Ile Ala His Tyr Leu His Leu
            115                 120                 125

Gly Pro Ile Cys Thr Leu Pro Asn Gln Thr Glu Thr Ile Pro Ala Pro
        130                 135                 140

Ile Val Asp Glu Ser Ser Gln Ser Phe Leu Leu Gln Gln Arg Arg
145                 150                 155                 160

Leu Ala Asp Lys Leu Lys Glu Arg Leu Gly Tyr Leu Gly Val Tyr Tyr
                165                 170                 175

Lys Arg Lys Pro Ser His Phe Tyr Arg Asn Phe Ser Pro Gln Glu Lys
            180                 185                 190

Gln Glu Tyr Leu Glu Asp Leu Ser Ser Gln Tyr Arg Glu Ile Ile Leu
        195                 200                 205

Ser Tyr Phe Ser Asp Glu Gly Thr Val Asn Asp Leu Leu Asp Gln Phe
210                 215                 220

Val Asn Gln Ala Phe Phe Ala Asp Leu Ala Ile Ser Gln Ile Leu Glu
225                 230                 235                 240

Ile His Met Glu Leu Met Asp Glu Phe Ser Gln His Leu Lys Leu Glu
                245                 250                 255

Gly Arg Ser Glu Glu Val Leu Leu Asp Tyr Arg Leu Val Leu Ile Asp
            260                 265                 270

Ile Leu Ala His Leu Gly Glu Met Tyr Arg Arg Ser Ile Pro Arg Glu
        275                 280                 285

Asp Ile Pro Phe Asp Val Tyr Tyr Gln Thr Asp
    290                 295

<210> SEQ ID NO 3
<211> LENGTH: 318
<212> TYPE: DNA
<213> ORGANISM: Synechocystis sp.PCC 6803

<400> SEQUENCE: 3
atgagcccct ttaaaaaaac ttacgttctc aaactctacg tagctggcaa cacccccaac      60
tctgtgcggg ccttaaaaat gctaaaaaat atccttgagc aagaattcca gggagtttat     120
gccctcaaag taatcgacgt gttgaaaaat ccccaattag ccgaagaaga taaaattctt     180
gccaccccca ccttggctaa atcctaccg ccccctgtca ggaaaatcat cggcgacctt      240
tccgaccgag agaaagtatt gattggttta gacctgctct atgacgaaat tcgggaacgg     300
gaagcagaag accaatag                                                  318

<210> SEQ ID NO 4
<211> LENGTH: 105
<212> TYPE: PRT
<213> ORGANISM: Synechocystis sp.PCC 6803

<400> SEQUENCE: 4

Met Ser Pro Phe Lys Lys Thr Tyr Val Leu Lys Leu Tyr Val Ala Gly
1               5                   10                  15

Asn Thr Pro Asn Ser Val Arg Ala Leu Lys Met Leu Lys Asn Ile Leu
            20                  25                  30

Glu Gln Glu Phe Gln Gly Val Tyr Ala Leu Lys Val Ile Asp Val Leu
        35                  40                  45

Lys Asn Pro Gln Leu Ala Glu Glu Asp Lys Ile Leu Ala Thr Pro Thr
    50                  55                  60
```

```
Leu Ala Lys Ile Leu Pro Pro Val Arg Lys Ile Ile Gly Asp Leu
 65                  70                  75                  80

Ser Asp Arg Glu Lys Val Leu Ile Gly Leu Asp Leu Leu Tyr Asp Glu
                 85                  90                  95

Ile Arg Glu Arg Glu Ala Glu Asp Gln
            100                 105

<210> SEQ ID NO 5
<211> LENGTH: 327
<212> TYPE: DNA
<213> ORGANISM: Synechocystis sp.PCC 6803

<400> SEQUENCE: 5
atggaaaatt taaacgctct atctggcaat caaaacttgg aagtttggca actgcgtctg     60
tatgtagcgg gacaaactcc taaatccgtc acagctttta taaatttaaa aaagatttgt    120
gaagaatatc taaacggtca ataccaaatt gaaatcatcg atttgaccca caacctgaa    180 ttggcgattg aagatagtat tttggcattg cctactttag taagaaaatt acccgaacca    240
atcaaaaaaa ttattggtga tttgtccaat acagaaaagg tattagtggg cttacaaatt    300
ttaccctcta tggattggaa aatctag                                       327

<210> SEQ ID NO 6
<211> LENGTH: 108
<212> TYPE: PRT
<213> ORGANISM: Synechocystis sp.PCC 6803

<400> SEQUENCE: 6

Met Glu Asn Leu Asn Ala Leu Ser Gly Asn Gln Asn Leu Glu Val Trp
 1               5                  10                  15

Gln Leu Arg Leu Tyr Val Ala Gly Gln Thr Pro Lys Ser Val Thr Ala
                20                  25                  30

Phe Ile Asn Leu Lys Lys Ile Cys Glu Glu Tyr Leu Asn Gly Gln Tyr
            35                  40                  45

Gln Ile Glu Ile Ile Asp Leu Thr Gln Gln Pro Glu Leu Ala Ile Glu
     50                  55                  60

Asp Ser Ile Leu Ala Leu Pro Thr Leu Val Arg Lys Leu Pro Glu Pro
 65                  70                  75                  80

Ile Lys Lys Ile Ile Gly Asp Leu Ser Asn Thr Glu Lys Val Leu Val
                 85                  90                  95

Gly Leu Gln Ile Leu Pro Ser Met Asp Trp Lys Ile
            100                 105

<210> SEQ ID NO 7
<211> LENGTH: 309
<212> TYPE: DNA
<213> ORGANISM: Synechocystis sp.PCC 6803

<400> SEQUENCE: 7
atggatatga ataggattgt gttaagactt tatatcacgg gtaattcggt gcgttctcag     60
caggcgatcg ccaatattta ccgcatttgc caagaagatc taggggatca gtacaatgtt    120
gaaatcattg acgtgttgga acagcctcaa cgggcggaag aggaaaaaat catggtcacc    180
cccaccttga tcaaacaatt gccccctccc ctacagcgga ttatcggcga tatgtccaat    240
acggaaaaag tttttgctggg attagatatt gtgcccgaag gttttgcaggt tcgtttgccg    300 gaggattaa                                                           309
```

```
<210> SEQ ID NO 8
<211> LENGTH: 102
<212> TYPE: PRT
<213> ORGANISM: Synechocystis sp.PCC 6803

<400> SEQUENCE: 8
```

Met Asp Met Asn Arg Ile Val Leu Arg Leu Tyr Ile Thr Gly Asn Ser
1               5                   10                  15

Val Arg Ser Gln Gln Ala Ile Ala Asn Ile Tyr Arg Ile Cys Gln Glu
            20                  25                  30

Asp Leu Gly Asp Gln Tyr Asn Val Glu Ile Ile Asp Val Leu Glu Gln
        35                  40                  45

Pro Gln Arg Ala Glu Glu Glu Lys Ile Met Val Thr Pro Thr Leu Ile
    50                  55                  60

Lys Gln Leu Pro Pro Pro Leu Gln Arg Ile Ile Gly Asp Met Ser Asn
65                  70                  75                  80

Thr Glu Lys Val Leu Leu Gly Leu Asp Ile Val Pro Glu Gly Leu Gln
                85                  90                  95

Val Arg Leu Pro Glu Asp
            100

```
<210> SEQ ID NO 9
<211> LENGTH: 1560
<212> TYPE: DNA
<213> ORGANISM: Synechocystis sp.PCC 6803

<400> SEQUENCE: 9
```

| | | | | | |
|---|---|---|---|---|---|
| atgaacttac | cgattgttaa | cgaacgtaat | cgccccgatg | tgccaaggaa | gggagtgcaa | 60 |
| aaaattcgta | ctgtgatcga | gggctttgac | gaaattaccc | acggcggttt | acccattggc | 120 |
| cgtacaaccc | tggtgagtgg | cacctccggc | acaggcaaaa | ctctcttggc | agtacaattt | 180 |
| ctttaccaag | gcattcacca | tttcgattat | ccgggtttat | tcattacatt | tgaagaatcc | 240 |
| cccagtgaca | ttattgaaaa | tgcctatagt | tttggctggg | atttacaaca | attaattgac | 300 |
| gatggcaaat | tgtttatcct | cgatgcttcc | cccgatccgg | aagggcagga | agtggtgggc | 360 |
| acctttgatc | tgtcggcctt | aattgaaaga | attcagtatg | cagtgcgaaa | atataaagcc | 420 |
| aagttagttt | ccattgattc | ggtcacagcg | gtatttcaac | aatatgatgc | ggcttcggtg | 480 |
| gtgcggcggg | aaatttttcg | tttggtggct | aggttaaaac | agctccaggt | aacgtccatt | 540 |
| atgaccaccg | aacgggtgga | agaatatggc | cccattgccc | gctttggcgt | agaggaattc | 600 |
| gtctccgata | acgtggtggt | tttgcgtaat | gttttagaag | gggaacggcg | acgacgcacg | 660 |
| gtggaaatcc | tcaaactacg | gggtaccacc | cacatgaagg | gggaatatcc | tttcactatc | 720 |
| acccacgacg | gcattaacat | ttttcccctg | ggagccatgc | gcctcaccca | gaggtcttcc | 780 |
| aatgcccgca | tttcatcggg | agtacaaacc | ttggacgaaa | tgtgtggcgg | tggcttttc | 840 |
| aaagattcga | ttattctggc | tacggggggct | actggtacgg | gcaaaaccct | gttggtaagc | 900 |
| aaatttttgc | aggaaggttg | tcgccaaaga | gaacgggcca | ttttgtttgc | ctatgaggaa | 960 |
| tccagggctc | agctttcccg | caacgcttct | tcctggggca | ttgattttga | agaaatggaa | 1020 |
| cacaagggtt | tattaaaaact | tctttgtacc | tatccagaat | cggcgggctt | ggaggatcat | 1080 |
| ttgcaaatga | tcaagtcgga | aatatcggaa | tttaaaccctt | cccgcattgc | cattgattcc | 1140 |
| ctttctgccc | tggccggggg | agtgaccaat | aatgctttcc | gtcaatttgt | cattggggta | 1200 |
| acgggctacg | ccaaacagga | ggagattact | ggcttcttta | ccaataccac | ggaccaattt | 1260 |
| atgggggccc | attccattac | ggaatcccat | atttccacca | ttacagacac | cattttgatg | 1320 |

```
ttgcagtatg tggaaatccg aggagaaatg tcccgggcat tgaatgtgtt taaaatgcgg    1380
ggttcctggc atgataaagg cattcgagaa tatagcatta gccatgatgg ccctgatatt    1440
cgcgattcct ccgcaatta tgagcggatt atcagtggtt cccccacccg cattagtgtg    1500
gatgaaaaat ctgagctttc ccgcattgtc cggggtgtta aggacaagac cgctgagtag    1560
```

<210> SEQ ID NO 10
<211> LENGTH: 519
<212> TYPE: PRT
<213> ORGANISM: Synechocystis sp.PCC 6803

<400> SEQUENCE: 10

```
Met Asn Leu Pro Ile Val Asn Glu Arg Asn Arg Pro Asp Val Pro Arg
1               5                   10                  15

Lys Gly Val Gln Lys Ile Arg Thr Val Ile Glu Gly Phe Asp Glu Ile
            20                  25                  30

Thr His Gly Gly Leu Pro Ile Gly Arg Thr Thr Leu Val Ser Gly Thr
        35                  40                  45

Ser Gly Thr Gly Lys Thr Leu Leu Ala Val Gln Phe Leu Tyr Gln Gly
    50                  55                  60

Ile His His Phe Asp Tyr Pro Gly Leu Phe Ile Thr Phe Glu Glu Ser
65                  70                  75                  80

Pro Ser Asp Ile Ile Glu Asn Ala Tyr Ser Phe Gly Trp Asp Leu Gln
                85                  90                  95

Gln Leu Ile Asp Asp Gly Lys Leu Phe Ile Leu Asp Ala Ser Pro Asp
            100                 105                 110

Pro Glu Gly Gln Glu Val Val Gly Thr Phe Asp Leu Ser Ala Leu Ile
        115                 120                 125

Glu Arg Ile Gln Tyr Ala Val Arg Lys Tyr Lys Ala Lys Leu Val Ser
    130                 135                 140

Ile Asp Ser Val Thr Ala Val Phe Gln Gln Tyr Asp Ala Ala Ser Val
145                 150                 155                 160

Val Arg Arg Glu Ile Phe Arg Leu Val Ala Arg Leu Lys Gln Leu Gln
                165                 170                 175

Val Thr Ser Ile Met Thr Thr Glu Arg Val Glu Glu Tyr Gly Pro Ile
            180                 185                 190

Ala Arg Phe Gly Val Glu Glu Phe Val Ser Asp Asn Val Val Val Leu
        195                 200                 205

Arg Asn Val Leu Glu Gly Glu Arg Arg Arg Thr Val Glu Ile Leu
    210                 215                 220

Lys Leu Arg Gly Thr Thr His Met Lys Gly Glu Tyr Pro Phe Thr Ile
225                 230                 235                 240

Thr His Asp Gly Ile Asn Ile Phe Pro Leu Gly Ala Met Arg Leu Thr
                245                 250                 255

Gln Arg Ser Ser Asn Ala Arg Ile Ser Ser Gly Val Gln Thr Leu Asp
            260                 265                 270

Glu Met Cys Gly Gly Gly Phe Phe Lys Asp Ser Ile Ile Leu Ala Thr
        275                 280                 285

Gly Ala Thr Gly Thr Gly Lys Thr Leu Leu Val Ser Lys Phe Leu Gln
    290                 295                 300

Glu Gly Cys Arg Gln Arg Glu Arg Ala Ile Leu Phe Ala Tyr Glu Glu
305                 310                 315                 320

Ser Arg Ala Gln Leu Ser Arg Asn Ala Ser Ser Trp Gly Ile Asp Phe
                325                 330                 335
```

```
Glu Glu Met Glu His Lys Gly Leu Leu Lys Leu Leu Cys Thr Tyr Pro
                340                 345                 350

Glu Ser Ala Gly Leu Glu Asp His Leu Gln Met Ile Lys Ser Glu Ile
            355                 360                 365

Ser Glu Phe Lys Pro Ser Arg Ile Ala Ile Asp Ser Leu Ser Ala Leu
        370                 375                 380

Ala Arg Gly Val Thr Asn Asn Ala Phe Arg Gln Phe Val Ile Gly Val
385                 390                 395                 400

Thr Gly Tyr Ala Lys Gln Glu Glu Ile Thr Gly Phe Phe Thr Asn Thr
                405                 410                 415

Thr Asp Gln Phe Met Gly Ala His Ser Ile Thr Glu Ser His Ile Ser
            420                 425                 430

Thr Ile Thr Asp Thr Ile Leu Met Leu Gln Tyr Val Glu Ile Arg Gly
        435                 440                 445

Glu Met Ser Arg Ala Leu Asn Val Phe Lys Met Arg Gly Ser Trp His
450                 455                 460

Asp Lys Gly Ile Arg Glu Tyr Ser Ile Ser His Asp Gly Pro Asp Ile
465                 470                 475                 480

Arg Asp Ser Phe Arg Asn Tyr Glu Arg Ile Ile Ser Gly Ser Pro Thr
                485                 490                 495

Arg Ile Ser Val Asp Glu Lys Ser Glu Leu Ser Arg Ile Val Arg Gly
            500                 505                 510

Val Lys Asp Lys Thr Ala Glu
        515
```

<210> SEQ ID NO 11
<211> LENGTH: 1707
<212> TYPE: DNA
<213> ORGANISM: Synechocystis sp.PCC 6803

<400> SEQUENCE: 11

```
atgacagata acagccaaag tctctctcta attaaatgcc ccaccgggat tcaaggtttt      60
gatgaaatta ccaacggtgg tttaccccag ggccgaccaa ccctcatttg tggttcagcc     120
ggttgtggta aaactctatt tggggtggaa ttttagtgc gggggcagt ggaatatgga      180
gagccagggg ttttagtttc ctttgaagaa agcgccaaag agatcattca aaatgtggcg     240
tccttagggt ggaatttaca agatttagtt gccgaagaaa aaattttaat tgatcatatt     300
tatgttgaag ctagcgaaat tcaagaaaca ggagaatatg acctcgaagc cctatttatt     360
cgcttaggct atgccattaa taaaattggt gcaaagcgaa tccttttaga tacaattgaa     420
gttctttttt ctggcttaga gaataccaat attgtccgag cagaattacg tcgtttattc     480
cattggttaa gcaaaaagg cgttaccgca gtgatcacag gggaacgggg cgacaaaaat     540
ttaactaggc aaggcctgga gaatacgtg tctgattgtg ttattaaact cgatcaaaaa     600
actgtggaag aggttgccac cagaactatt caggtcgtta atatcgagg ctcacgccat     660
agcaataatg aatatccttt tttgatcgaa gaaaatggca tttccgtgtt gcctatcact     720
tccctgattc tcaatcacag cgtctcccag gagcgaattt ccactggcat tccccaattg     780
gatgatatgt ttggcgggca gggttattac cgtggcagta gcattttagt aaccgggaga     840
gctggcactg gcaaaactac cctggcggcc ttttttgccc aggcaacttg cttacgggga     900
gaacgatgtt tatatcttgc taccgaagaa tcgcccaac aaatttgccg caatttaaat     960
tccattggtc tagatttatc gccctattta gacagccaat tactacaatt tgatgccact    1020
```

-continued

```
cgtcctacta attataattt agagatgcgt ctgtttaaga ttcatagttg ggtcaggaat    1080
tttaagccaa gcttggtggt agttgatcca atgagtaacc taattactag tggcaattta    1140
aatcaaacaa aaaactttt catgcgtcta attgattatc taaaaagcca aaagattacc     1200 gtattttga cggatttgac cggcggcaat gtgggatatg ataatgaaca acagaagtt      1260 ggtgtttctt ccttaatgga tacatggctg gagttacaga ccctgagaat aaatggagaa    1320
agaaatcgta ttctctatat tttgaaatct aggggcatgg cccactccaa ccaagtgcgg    1380
gaattcatcc ttagtaatga tggggtagat ttgattgaag cttatattgg tgaagggcaa    1440
gtactaacag gtacccaaag gattaatcaa attttagaag aagaggcgat cgccaaaagg    1500
cggcaacagg ccctagaact cagcaaacgg aattttgagc gaaaaaagta cttactgcag    1560
gcgaagattg atgccctcca aatgaaacta gccagtcaag atgaggaatt agaagtacta    1620
atgttagagg agaaagaatt caaacaaaca atgttggcca accgtaatct gattaaaaag    1680
tctcgccaca tttatcaaaa cccctaa                                       1707
```

<210> SEQ ID NO 12
<211> LENGTH: 568
<212> TYPE: PRT
<213> ORGANISM: Synechocystis sp.PCC 6803

<400> SEQUENCE: 12

```
Met Thr Asp Asn Ser Gln Ser Leu Ser Leu Ile Lys Cys Pro Thr Gly
1               5                   10                  15

Ile Gln Gly Phe Asp Glu Ile Thr Asn Gly Gly Leu Pro Gln Gly Arg
            20                  25                  30

Pro Thr Leu Ile Cys Gly Ser Ala Gly Cys Gly Lys Thr Leu Phe Gly
        35                  40                  45

Val Glu Phe Leu Val Arg Gly Ala Val Glu Tyr Gly Glu Pro Gly Val
    50                  55                  60

Leu Val Ser Phe Glu Glu Ser Ala Lys Glu Ile Ile Gln Asn Val Ala
65                  70                  75                  80

Ser Leu Gly Trp Asn Leu Gln Asp Leu Val Ala Glu Lys Ile Leu
            85                  90                  95

Ile Asp His Ile Tyr Val Glu Ala Ser Glu Ile Gln Glu Thr Gly Glu
            100                 105                 110

Tyr Asp Leu Glu Ala Leu Phe Ile Arg Leu Gly Tyr Ala Ile Asn Lys
        115                 120                 125

Ile Gly Ala Lys Arg Ile Leu Leu Asp Thr Ile Glu Val Leu Phe Ser
    130                 135                 140

Gly Leu Glu Asn Thr Asn Ile Val Arg Ala Glu Leu Arg Arg Leu Phe
145                 150                 155                 160

His Trp Leu Lys Gln Lys Gly Val Thr Ala Val Ile Thr Gly Glu Arg
            165                 170                 175

Gly Asp Lys Asn Leu Thr Arg Gln Gly Leu Glu Glu Tyr Val Ser Asp
        180                 185                 190

Cys Val Ile Lys Leu Asp Gln Lys Thr Val Glu Glu Val Ala Thr Arg
    195                 200                 205

Thr Ile Gln Val Val Lys Tyr Arg Gly Ser Arg His Ser Asn Asn Glu
    210                 215                 220

Tyr Pro Phe Leu Ile Glu Glu Asn Gly Ile Ser Val Leu Pro Ile Thr
225                 230                 235                 240

Ser Leu Ile Leu Asn His Ser Val Ser Gln Glu Arg Ile Ser Thr Gly
            245                 250                 255
```

```
Ile Pro Gln Leu Asp Asp Met Phe Gly Gly Gln Gly Tyr Tyr Arg Gly
            260                 265                 270

Ser Ser Ile Leu Val Thr Gly Arg Ala Gly Thr Gly Lys Thr Thr Leu
        275                 280                 285

Ala Ala Phe Phe Ala Gln Ala Thr Cys Leu Arg Gly Glu Arg Cys Leu
290                 295                 300

Tyr Leu Ala Thr Glu Glu Ser Pro Gln Gln Ile Cys Arg Asn Leu Asn
305                 310                 315                 320

Ser Ile Gly Leu Asp Leu Ser Pro Tyr Leu Asp Ser Gln Leu Leu Gln
                325                 330                 335

Phe Asp Ala Thr Arg Pro Thr Asn Tyr Asn Leu Glu Met Arg Leu Phe
            340                 345                 350

Lys Ile His Ser Trp Val Arg Asn Phe Lys Pro Ser Leu Val Val Val
        355                 360                 365

Asp Pro Met Ser Asn Leu Ile Thr Ser Gly Asn Leu Asn Gln Thr Lys
370                 375                 380

Asn Phe Phe Met Arg Leu Ile Asp Tyr Leu Lys Ser Gln Lys Ile Thr
385                 390                 395                 400

Val Phe Leu Thr Asp Leu Thr Gly Gly Asn Val Gly Tyr Asp Asn Glu
                405                 410                 415

Gln Thr Glu Val Gly Val Ser Ser Leu Met Asp Thr Trp Leu Glu Leu
            420                 425                 430

Gln Thr Leu Arg Ile Asn Gly Glu Arg Asn Arg Ile Leu Tyr Ile Leu
        435                 440                 445

Lys Ser Arg Gly Met Ala His Ser Asn Gln Val Arg Glu Phe Ile Leu
450                 455                 460

Ser Asn Asp Gly Val Asp Leu Ile Glu Ala Tyr Ile Gly Glu Gly Gln
465                 470                 475                 480

Val Leu Thr Gly Thr Gln Arg Ile Asn Gln Ile Leu Glu Glu Ala
                485                 490                 495

Ile Ala Lys Arg Arg Gln Ala Leu Glu Leu Ser Lys Arg Asn Phe
                500                 505                 510

Glu Arg Lys Lys Tyr Leu Leu Gln Ala Lys Ile Asp Ala Leu Gln Met
            515                 520                 525

Lys Leu Ala Ser Gln Asp Glu Glu Leu Glu Val Leu Met Leu Glu Glu
530                 535                 540

Lys Glu Phe Lys Gln Thr Met Leu Ala Asn Arg Asn Leu Ile Lys Lys
545                 550                 555                 560

Ser Arg His Ile Tyr Gln Asn Pro
                565
```

<210> SEQ ID NO 13
<211> LENGTH: 1518
<212> TYPE: DNA
<213> ORGANISM: Synechocystis sp.PCC 6803

<400> SEQUENCE: 13

```
atgatcgacc aagagacaga tggcattgag aagtttggaga cgggtattcc aggctttgat      60
tttctgtccg acggtggtct ccccctcggc cgcgccaccc taattgccgg cacagcaggt     120
agtgctaaaa ctattttgc ttcccaattt ttagtcgaag gtattcagcg gggggaaaac      180 ggtgttttg tcacttttga ggaacccccc aaggccctac ggaaaaatat gcggggtttt      240
ggttgggata ttcaacaatg ggaaaacgaa ggtaaatggg tttttgtcga tgcttccccc      300
```

```
caaccaggcg atcgccccat tgtcagcggt gaatatgacc tagggggcctt gattgcccgc    360
attgaacacg ctgtccgtaa atataaagcc agtcgcattt ccctcgattc cctgggggca    420
atttttagtc acctcagtga cagtgcccag gtgcgcagtg acctattccg cttggcctct    480
gccctccggg aactgggagt caccgccatt atgaccgccg aacgggtgga agaatacggt    540
gaaattagcc gttacggagt ggaagaattt gttgctgata acgtggtcat tgtccgcaac    600
gtcctcgccg atgaaaaacg tcgtcgcacc atcgagatcc ttaaataccg tggcaccgac    660
caccaaaagg gcgaatttcc cttcactatc attaataaaa aaggcatcgt catcattccc    720
ctgtcggcga tcgagctgga gcaaaaatcc tccgacatcc gcatcacctc cggcagtgaa    780
gaattagacc gcatgtgtgg cagtggcttc ttccgggatt cgattatttt agtctccggg    840
gcaacgggta ctggtaaaac cctgatggtg acggagttta tggacggcgg cgtgccaat    900
ggagagcgct gtttagtttt tgcctttgag gaaagtcgag aacaattaat tcgcaatgcc    960
accggctggg gggtagattt caaacaaatg gaaaaggaag gcaaactaaa agtggtttgt   1020
cgctatccag aaaccaccaa cttggaaaac cacctgatca tgatgaagga tattatccaa   1080
gaatttaagc ccaatcgggt ggcggtggac agtctttctg ccctagaacg ggtttccacc   1140
ctaaaaagtt ttcgcgaatt tattattggc ttaacttcct ttattaaaca acaggaaatt   1200
ggtggtttat tcacttccac taccccccaat ttactagggg gagcttccat taccgatgcc   1260
catatttcca ccattaccga ttcgattatt cttttgcgtt acgtggaaat gtatggcgaa   1320
atgcgccggg gaattacggt gctaaagatg cggggttcta tgcacgacaa agatatccgg   1380
gaattttcca ttgaccatca agggatgcac attggtaaac ctttccgtaa tgtcaccggc   1440
attctggccg gaccccccat gtacacagcc cagagtgagg tggaaagatt gagcggttta   1500
ttcgatgaga aaatatag                                                   1518
```

<210> SEQ ID NO 14
<211> LENGTH: 505
<212> TYPE: PRT
<213> ORGANISM: Synechocystis sp.PCC 6803

<400> SEQUENCE: 14

```
Met Ile Asp Gln Glu Thr Asp Gly Ile Glu Lys Leu Glu Thr Gly Ile
1               5                   10                  15

Pro Gly Phe Asp Phe Leu Ser Asp Gly Gly Leu Pro Leu Gly Arg Ala
            20                  25                  30

Thr Leu Ile Ala Gly Thr Ala Gly Ser Ala Lys Thr Ile Phe Ala Ser
        35                  40                  45

Gln Phe Leu Val Glu Gly Ile Gln Arg Gly Glu Asn Gly Val Phe Val
    50                  55                  60

Thr Phe Glu Glu Pro Pro Lys Ala Leu Arg Lys Asn Met Arg Gly Phe
65                  70                  75                  80

Gly Trp Asp Ile Gln Gln Trp Glu Asn Glu Gly Lys Trp Val Phe Val
                85                  90                  95

Asp Ala Ser Pro Gln Pro Gly Asp Arg Pro Ile Val Ser Gly Glu Tyr
            100                 105                 110

Asp Leu Gly Ala Leu Ile Ala Arg Ile Glu His Ala Val Arg Lys Tyr
        115                 120                 125

Lys Ala Ser Arg Ile Ser Leu Asp Ser Leu Gly Ala Ile Phe Ser His
    130                 135                 140

Leu Ser Asp Ser Ala Gln Val Arg Ser Asp Leu Phe Arg Leu Ala Ser
145                 150                 155                 160
```

Ala Leu Arg Glu Leu Gly Val Thr Ala Ile Met Thr Ala Glu Arg Val
            165                 170                 175

Glu Glu Tyr Gly Glu Ile Ser Arg Tyr Gly Val Glu Phe Val Ala
        180                 185                 190

Asp Asn Val Val Ile Val Arg Asn Val Leu Ala Asp Glu Lys Arg Arg
            195                 200                 205

Arg Thr Ile Glu Ile Leu Lys Tyr Arg Gly Thr Asp His Gln Lys Gly
210                 215                 220

Glu Phe Pro Phe Thr Ile Ile Asn Lys Lys Gly Ile Val Ile Ile Pro
225                 230                 235                 240

Leu Ser Ala Ile Glu Leu Glu Gln Lys Ser Ser Asp Ile Arg Ile Thr
            245                 250                 255

Ser Gly Ser Glu Glu Leu Asp Arg Met Cys Gly Ser Gly Phe Phe Arg
            260                 265                 270

Asp Ser Ile Ile Leu Val Ser Gly Ala Thr Gly Thr Gly Lys Thr Leu
            275                 280                 285

Met Val Thr Glu Phe Met Asp Gly Val Ala Asn Gly Glu Arg Cys
            290                 295                 300

Leu Val Phe Ala Phe Glu Glu Ser Arg Glu Gln Leu Ile Arg Asn Ala
305                 310                 315                 320

Thr Gly Trp Gly Val Asp Phe Lys Gln Met Glu Lys Glu Gly Lys Leu
            325                 330                 335

Lys Val Val Cys Arg Tyr Pro Glu Thr Thr Asn Leu Glu Asn His Leu
            340                 345                 350

Ile Met Met Lys Asp Ile Ile Gln Glu Phe Lys Pro Asn Arg Val Ala
            355                 360                 365

Val Asp Ser Leu Ser Ala Leu Glu Arg Val Ser Thr Leu Lys Ser Phe
370                 375                 380

Arg Glu Phe Ile Ile Gly Leu Thr Ser Phe Ile Lys Gln Gln Glu Ile
385                 390                 395                 400

Gly Gly Leu Phe Thr Ser Thr Thr Pro Asn Leu Leu Gly Gly Ala Ser
            405                 410                 415

Ile Thr Asp Ala His Ile Ser Thr Ile Thr Asp Ser Ile Ile Leu Leu
            420                 425                 430

Arg Tyr Val Glu Met Tyr Gly Glu Met Arg Arg Gly Ile Thr Val Leu
            435                 440                 445

Lys Met Arg Gly Ser Met His Asp Lys Asp Ile Arg Glu Phe Ser Ile
450                 455                 460

Asp His Gln Gly Met His Ile Gly Lys Pro Phe Arg Asn Val Thr Gly
465                 470                 475                 480

Ile Leu Ala Gly Thr Pro Met Tyr Thr Ala Gln Ser Glu Val Glu Arg
            485                 490                 495

Leu Ser Gly Leu Phe Asp Glu Lys Ile
            500                 505

<210> SEQ ID NO 15
<211> LENGTH: 26
<212> TYPE: DNA
<213> ORGANISM: Artificial
<220> FEATURE:
<223> OTHER INFORMATION: primer

<400> SEQUENCE: 15
attattcata tgcagtctcc cctctc                                          26

<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16
aaacccgtta acttaatccg tctgataata                              30

<210> SEQ ID NO 17
<211> LENGTH: 27
<212> TYPE: DNA
<213> ORGANISM: Artificial
<220> FEATURE:
<223> OTHER INFORMATION: primer

<400> SEQUENCE: 17
attattcata tgagccccct taaaaaa                                 27

<210> SEQ ID NO 18
<211> LENGTH: 30
<212> TYPE: DNA
<213> ORGANISM: Artificial
<220> FEATURE:
<223> OTHER INFORMATION: primer

<400> SEQUENCE: 18
aaacccgtta acctattggt cttctgcttc                              30

<210> SEQ ID NO 19
<211> LENGTH: 27
<212> TYPE: DNA
<213> ORGANISM: Artificial
<220> FEATURE:
<223> OTHER INFORMATION: primer

<400> SEQUENCE: 19
attattcata tggaaaattt aaacgct                                 27

<210> SEQ ID NO 20
<211> LENGTH: 30
<212> TYPE: DNA
<213> ORGANISM: Artificial
<220> FEATURE:
<223> OTHER INFORMATION: primer

<400> SEQUENCE: 20
aaacccgtta acctagattt tccaatccat                              30

<210> SEQ ID NO 21
<211> LENGTH: 27
<212> TYPE: DNA
<213> ORGANISM: Artificial
<220> FEATURE:
<223> OTHER INFORMATION: primer

<400> SEQUENCE: 21
attattcata tggatatgaa taggatt                                 27

<210> SEQ ID NO 22
<211> LENGTH: 30
<212> TYPE: DNA
<213> ORGANISM: Artificial
<220> FEATURE:
<223> OTHER INFORMATION: primer

```
<400> SEQUENCE: 22
aaacccgtta acttaatcct ccggcaaacg                                          30

<210> SEQ ID NO 23
<211> LENGTH: 27
<212> TYPE: DNA
<213> ORGANISM: Artificial
<220> FEATURE:
<223> OTHER INFORMATION: primer

<400> SEQUENCE: 23
attattcata tgaacttacc gattgtt                                             27

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24 aaagggata tcctactcag cggtcttgtc                                           30

<210> SEQ ID NO 25
<211> LENGTH: 27
<212> TYPE: DNA
<213> ORGANISM: Artificial
<220> FEATURE:
<223> OTHER INFORMATION: primer

<400> SEQUENCE: 25
attattcata tgacagataa cagccaa                                             27

<210> SEQ ID NO 26
<211> LENGTH: 31
<212> TYPE: DNA
<213> ORGANISM: Artificial
<220> FEATURE:
<223> OTHER INFORMATION: primer

<400> SEQUENCE: 26
aaaggggtta acttaggggt tttgataaat g                                        31

<210> SEQ ID NO 27
<211> LENGTH: 27
<212> TYPE: DNA
<213> ORGANISM: Artificial
<220> FEATURE:
<223> OTHER INFORMATION: primer

<400> SEQUENCE: 27
attattcata tgatcgacca agagaca                                             27

<210> SEQ ID NO 28
<211> LENGTH: 30
<212> TYPE: DNA
<213> ORGANISM: Artificial
<220> FEATURE:
<223> OTHER INFORMATION: primer

<400> SEQUENCE: 28
aaaggggtta acctatattt tctcatcgaa                                          30
```

US 9,783,581 B2

METHOD FOR PRODUCING PLASTIC RAW MATERIAL FROM BLUE-GREEN ALGAE

RELATED APPLICATIONS

This application is a national stage application filed under 35 USC 371 of PCT/JP2015/052457, filed Jan. 29, 2015, which claims the benefit of Japanese Patent Application No. 2014-015560, filed Jan. 30, 2014, all of which are incorporated herein, in entirety, by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 11924400099.txt The size of the text file is 31 KB, and the text file was created on Jul. 26, 2016.

TECHNICAL FIELD

The present invention relates to blue-green algae overexpressing a clock protein gene and a method for producing organic acids, particularly organic acids that serve as raw materials of plastics, using the blue-green algae.

BACKGROUND ART

Polyhydroxybutyric acid (PHB) is a kind of biopolymer produced by microorganisms. As a microbially degradable thermoplastic resin, it is expected to serve as a material that can be applied to a wide range of fields such as pharmaceuticals, agricultural chemicals, medical materials, and industrial materials. PHB is a kind of polyhydroxyalkanoic acid (PHA), and is a polyester synthesized from acetyl-CoA via three-step reactions. Various methods of microbial production of PHA have so far been disclosed. For example, Patent Document 1 discloses a production method of PHB. However, all of those methods have their drawbacks in terms of requiring an organic carbon source as the assimilable carbon source.

Under the foregoing circumstances, various methods of efficient microbial production of PHA without requiring a reducing substance of an organic carbon source have been searched for. Although a number of studies on blue-green algae PHA have so far been reported, a locally increased enzyme activity has been shown not to result in an increase in the amount of PHA (Non Patent Document 1). In order to further increase the amount of PHA, the carbon metabolism needs to be drastically modified to drive the metabolic flow toward PHA. However, it has also been shown that modification of individual metabolic enzymes does not lead to the modification of the entire metabolism. Further, although the inhibition of sugar catabolism by the clock protein gene is reported in blue-green algae belonging to genus *Anabaena*, the algae do not have the ability to produce PHA, and thus there has been no report about the utilization of the algae in a production of PHA (Non Patent Document 2).

Among other organic acids, particularly succinic acid and lactic acid are known as raw materials of plastics, and from the environmental as well as economic points of view, there has been a demand for the establishment of a biological production system of these acids. While succinic acid is mainly synthesized from petroleum, recently startup companies engaged in a bio-based production of succinic acid have been established abroad. In light of this, inexpensive, environmentally-friendly production technology of succinic acid will directly bring benefits to society. According to the conventional method, succinic acid is produced through fermentation by heterotrophic bacteria using plant-derived carbohydrates. Meanwhile, there is concern about the stable supply of plant-derived carbohydrates due to their competition with food, unsettled weather, price hike, and so on.

PRIOR ART DOCUMENTS

Patent Documents

Patent Document 1: JP Patent Publication (Kokai) No. 1-222788 A (1989)

Non Patent Documents

Non Patent Document 1: International Journal of Biological Macromolecules, 30, 2002, 97 to 104
Non Patent Document 2: The Journal of Biological Chemistry, vol. 286, 44, 2011, 38109 to 38114

SUMMARY OF INVENTION

Problem to be Solved by the Invention

An object of the present invention is to increase a production amount of organic acids by constructing a system that enables efficient production of organic acids using blue-green algae, which are photosynthetic microorganisms, with utilizing carbon dioxide.

Means for Solving the Problem

The present inventors successfully increased a production amount of organic acids by overexpressing kaiABC genes, which are clock proteins, in blue-green algae.

That is, the present invention encompasses the following inventions.
(1) Blue-green algae overexpressing a clock protein gene.
(2) The blue-green algae according to (1), wherein the clock protein gene is kaiB gene or kaiC gene.
(3) The blue-green algae according to (1) or (2), wherein the blue-green algae has an ability to produce polyhydroxyalkanoic acid.
(4) The blue-green algae according to any of (1) to (3), wherein the blue-green algae has phaAB gene and phaEC gene.
(5) The blue-green algae according to any of (1) to (4), wherein the blue-green algae belongs to genus *Synechocystis*.
(6) A method for producing an organic acid, comprising culturing blue-green algae overexpressing a clock protein gene and collecting an organic acid.
(7) The method according to (6), wherein the organic acid is polyhydroxyalkanoic acid, the blue-green algae has an ability to produce polyhydroxyalkanoic acid, and the clock protein gene is kaiB gene or kaiC gene.
(8) The method according to (7), wherein the blue-green algae has phaAB gene and phaEC gene.
(9) The method according to (7) or (8), wherein the polyhydroxyalkanoic acid is polyhydroxybutyric acid.
(10) The method according to (6), wherein the organic acid is succinic acid or lactic acid and the clock protein gene is kaiB gene or kaiC gene.
(11) The method according to any of (6) to (10), wherein the blue-green algae belongs to genus *Synechocystis*.

(12) The method according to any of (6) to (11), wherein the culture is performed under nitrogen-deficient conditions.
(13) A method for enhancing an ability to produce an organic acid in blue-green algae, comprising overexpressing a clock protein gene in the blue-green algae.
(14) The method according to (13), wherein the organic acid is polyhydroxyalkanoic acid, the clock protein gene is kaiB gene or kaiC gene, and the blue-green algae has phaAB gene and phaEC gene.
(15) The method according to (14), wherein the polyhydroxyalkanoic acid is polyhydroxybutyric acid.
(16) The method according to (13), wherein the organic acid is polyhydroxyalkanoic acid and the clock protein gene is kaiB gene or kaiC gene.
(17) The method according to any of (13) to (16), wherein the blue-green algae belongs to genus *Synechocystis*.
(18) The method according to any of (13) to (17), wherein the culture is performed under nitrogen-deficient conditions.

This specification incorporates the content of the specification of Japanese Patent Application No. 2014-015560, for which priority is claimed to the present application.

Effects of the Invention

The present invention enables the efficient production of organic acids including polyhydroxyalkanoic acid, succinic acid, and lactic acid using blue-green algae, which are photosynthetic microorganisms, with utilizing carbon dioxide.

BRIEF DESCRIPTION OF DRAWINGS

The present invention is characterized by overexpressing of a clock protein gene in blue-green algae.

In the present invention, a clock protein refers to a protein that generates the circadian rhythm, which is a physiological phenomenon that oscillates with a cycle of approximately 24 hours. Also, a clock protein gene refers to a gene encoding a clock protein. In the narrow sense, with respect to blue-green algae, the clock protein gene refers to the following three genes, namely kaiA, kaiB, and kaiC genes and their homologous genes. The kaiA gene is associated with phosphorylation of KaiC. The kaiB gene promotes dephosphorylation of KaiC. The kaiC gene has activities of self-phosphorylation and dephosphorylation, and the phosphorylation reactions are known to occur on a 24-hour cycle.

PhaA gene refers to a gene encoding β-ketothiolase, which synthesizes acetoacetyl-CoA from acetyl-CoA. PhaB gene refers to a gene encoding acetoacetyl-CoA reductase, which synthesizes 3-hydroxybutyryl-CoA from acetoacetyl-CoA. PhaC gene refers to a gene encoding a subunit of PHA synthase, which synthesizes PHB from 3-hydroxybutyryl-CoA. PhaE gene refers to a gene encoding a subunit of PHA synthase, which synthesizes PHB from 3-hydroxybutyryl-CoA.

Further, the overexpression of a gene means that the amount of mRNA is increased compared to the wild type, preferably two time or more, more preferably three times or more, and even more preferably five times or more as much as the wild type.

Blue-green algae are a group of eubacteria that are alternatively called cyanobacteria, and are characterized by producing oxygen by photosynthesis. Blue-green algae may exist as single suspension cells, form a cluster of a small number of cells, or have a structure in which cells are arranged in a filamentous form, or exist in other forms. Although no particular limitation is imposed, blue-green algae existing as single cells are preferable.

The organic acids of the present invention particularly encompass, among other compounds found in a living body, carboxylic acids or compounds exhibiting acidity. Examples of the organic acids include polyhydroxyalkanoic acid, succinic acid, lactic acid, or acetic acid.

From the viewpoint of increasing the production amount of organic acids, it is preferable to use blue-green algae having an ability to produce organic acids, preferably polyhydroxyalkanoic acid, succinic acid, lactic acid, or acetic acid.

From the viewpoint of increasing the production amount of polyhydroxyalkanoic acid, it is preferable to use blue-green algae having ane ability to produce polyhydroxyalkanoic acid, preferably polyhydroxybutyric acid. Accordingly, it is preferable to use blue-green algae having a polyhydroxyalkanoic acid synthase gene, for example, phaAB gene and phaEC gene. The blue-green algae having the ability to produce polyhydroxyalkanoic acid encompass blue-green algae that are given the ability to produce polyhydroxyalkanoic acid through gene modification, mutation induction, and the like. Accordingly, blue-green algae having a polyhydroxyalkanoic acid synthase gene, for example, phaAB gene and phaEC gene also encompass blue-green algae into which a polyhydroxyalkanoic acid synthase gene is introduced.

From the viewpoint of increasing the production amount of succinic acid, it is preferable to use blue-green algae having an ability to produce succinic acid. Accordingly, it is preferable to use blue-green algae having a succinic acid synthase gene, for example a lactic acid dehydrogenase gene (ddh, ldh). Here, ldh and ddh refer to genes encoding enzymes acting to catalyze interconversion between lactic acid and pyruvic acid. The blue-green algae having an ability to produce succinic acid encompass blue-green algae that are given the ability to produce succinic acid through gene modification, mutation induction, and the like. Accordingly, the blue-green algae having a succinic acid synthase gene also encompass blue-green algae into which a succinic acid synthase gene is introduced.

From the viewpoint of increasing the production amount of lactic acid, it is preferable to use blue-green algae having an ability to produce lactic acid. Accordingly, it is preferable to use blue-green algae having a lactic acid synthase gene, for example a lactic acid dehydrogenase gene (ddh, ldh). The blue-green algae having an ability to produce lactic acid encompass blue-green algae that are given the ability to produce lactic acid through gene modification, mutation induction, and the like. Accordingly, the blue-green algae having a lactic acid synthase gene also encompass blue-green algae into which a lactic acid synthase gene is introduced.

From the viewpoint of increasing the production amount of acetic acid, it is preferable to use blue-green algae having an ability to produce acetic acid. Accordingly, it is preferable to use blue-green algae having an acetic acid synthase gene, for example acetyl-CoA synthase (acs), acetate kinase (ackA), aldehyde dehydrogenase, and acylphosphatase genes. The blue-green algae having an ability to produce acetic acid encompass blue-green algae that are given the ability to produce acetic acid through gene modification, mutation induction, and the like. Accordingly, the blue-green algae having an acetic acid synthase gene also encompass blue-green algae into which an acetic acid synthase gene is introduced.

Specific examples of blue-green algae include: blue-green algae belonging to genus *Synechocystis*; blue-green algae belonging to genus *Microcystis* such as *Microcystis aeruginosa*; blue-green algae belonging to genus *Arthrospira* such as *Arthrospira platensis*; blue-green algae belonging to genus *Cyanothece*; blue-green algae belonging to genus *Anabaena*; blue-green algae belonging to genus *Synechococcus*; blue-green algae belonging to genus *Thermosynechococcus* such as *Thermosynechococcus elongats*; blue-green algae belonging to genus *Gloeobacter* such as *Gloeobacter violaceus*; blue-green algae belonging to genus *Acaryochloris* such as *Acaryochloris marina*; blue-green algae belonging to genus *Nostoc* such as *Nostoc punctiforme*; blue-green algae belonging to genus *Trichodesmium*; blue-green algae belonging to genus *Prochloron*; and blue-green algae belonging to genus *Prochlorococcus*.

Among the aforementioned blue-green algae, at least blue-green algae belonging to genus *Synechocystis* such as *Synechocystis* sp. PCC 6803, blue-green algae belonging to genus *Microcystis* such as *Microcystis aeruginosa*, blue-green algae belonging to genus *Arthrospira* such as *Arthrospira platensis*, blue-green algae belonging to genus *Synechococcus*, blue-green algae belonging to genus *Cyanothece*, blue-green algae belonging to genus *Nostoc* such as *Nostoc muscorum* have been revealed to have the polyhydroxyalkanoic acid synthase gene.

Further, at least blue-green algae belonging to genus *Synechocystis* such as *Synechocystis* sp. PCC 6803, blue-green algae belonging to genus *Microcystis* such as *Microcystis aeruginosa*, blue-green algae belonging to genus *Arthrospira* such as *Arthrospira platensis*, blue-green algae belonging to genus *Cyanothece*, blue-green algae belonging to genus *Anabaena*, blue-green algae belonging to genus *Synechococcus*, blue-green algae belonging to genus *Thermosynechococcus* such as *Thermosynechococcus elongats*, blue-green algae belonging to genus *Gloeobacter* such as *Gloeobacter violaceus*, blue-green algae belonging to genus *Acaryochloris* such as *Acaryochloris marina*, blue-green algae belonging to genus *Nostoc* such as *Nostoc punctiforme*, blue-green algae belonging to genus *Trichodesmium*, blue-green algae belonging to genus *Prochloron*, blue-green algae belonging to genus *Prochlorococcus*, and the like have been revealed to have a succinic acid synthase gene.

Also, at least blue-green algae belonging to genus *Synechocystis* such as *Synechocystis* sp. PCC 6803, blue-green algae belonging to genus *Microcystis* such as *Microcystis aeruginosa*, blue-green algae belonging to genus *Arthrospira* such as *Arthrospira platensis*, blue-green algae belonging to genus *Cyanothece*, blue-green algae belonging to genus *Anabaena*, blue-green algae belonging to genus *Synechococcus*, blue-green algae belonging to genus *Thermosynechococcus* such as *Thermosynechococcus elongats*, blue-green algae belonging to genus *Gloeobacter* such as *Gloeobacter violaceus*, blue-green algae belonging to genus *Acaryochloris* such as *Acaryochloris marina*, blue-green algae belonging to genus *Nostoc* such as *Nostoc punctiforme*, blue-green algae belonging to genus *Trichodesmium*, blue-green algae belonging to genus *Prochloron*, blue-green algae belonging to genus *Prochlorococcus*, and the like have been revealed to have a lactic acid synthase gene.

Also, at least blue-green algae belonging to genus *Synechocystis* such as *Synechocystis* sp. PCC 6803, blue-green algae belonging to genus *Microcystis* such as *Microcystis aeruginosa*, blue-green algae belonging to genus *Arthrospira* such as *Arthrospira platensis*, blue-green algae belonging to genus *Cyanothece*, blue-green algae belonging to genus *Anabaena*, blue-green algae belonging to genus *Synechococcus*, blue-green algae belonging to genus *Thermosynechococcus* such as *Thermosynechococcus elongats*, blue-green algae belonging to genus *Gloeobacter* such as *Gloeobacter violaceus*, blue-green algae belonging to genus *Acaryochloris* such as *Acaryochloris marina*, blue-green algae belonging to genus *Nostoc* such as *Nostoc punctiforme*, blue-green algae belonging to genus *Trichodesmium*, blue-green algae belonging to genus *Prochloron*, blue-green algae belonging to genus *Prochlorococcus*, and the like have been revealed to have an acetic acid synthase gene.

In blue-green algae, clock gene cluster kaiABC is known as a gene of the biological clock. The clock gene cluster kaiABC consists of two operons, namely kaiA and kaiBC. The expression of the kaiBC operon is promoted by clock protein KaiA, and is suppressed by another clock protein KaiC. This is considered to be the feedback control of biological clock in blue-green algae. Further, KaiC is known to be phosphorylated, and the phosphorylation of KaiC has been revealed to be promoted by KaiA.

As specific examples of kaiA gene, which is a clock protein gene derived from blue-green algae, the nucleotide sequence and the amino acid sequence of the kaiA gene derived from *Synechocystis* sp. PCC 6803 are shown in SEQ ID NO: 1 and SEQ ID NO: 2, respectively. As specific examples of clock protein kaiB gene derived from blue-green algae, the nucleotide sequence and the amino acid sequence of kaiB1 gene derived from *Synechocystis* sp. PCC 6803 are shown in SEQ ID NO: 3 and SEQ ID NO: 4, respectively, the nucleotide sequence and the amino acid sequence of kaiB2 gene derived from the same are shown in SEQ ID NO: 5 and SEQ ID NO: 6, respectively, and the nucleotide sequence and the amino acid sequence of kaiB3 gene derived from the same are shown in SEQ ID NO: 7 and SEQ ID NO: 8, respectively. As specific examples of clock protein kaiC gene derived from blue-green algae, the nucleotide sequence and the amino acid sequence of kaiC1 gene derived from *Synechocystis* sp. PCC 6803 are shown in SEQ ID NO: 9 and SEQ ID NO: 10, respectively, the nucleotide sequence and the amino acid sequence of kaiC2 gene derived from the are shown in SEQ ID NO: 11 and SEQ ID NO: 12, respectively, and the nucleotide sequence and the amino acid sequence of kaiC3 gene derived therefrom are shown in SEQ ID NO: 13 and SEQ ID NO: 14, respectively.

The aforementioned kaiA gene, kaiB1 gene, kaiB2 gene, kaiB3 gene, kaiC1 gene, kaiC2 gene, and kaiC3 gene each encompass genes that are functionally equivalent to the genes consisting of the nucleotide sequences shown in SEQ ID NOs: 1, 3, 5, 7, 9, 11, and 13, respectively. Examples of the genes that are functionally equivalent to the genes consisting of the nucleotide sequences shown in SEQ ID NO: 1, 3, 5, 7, 9, 11, and 13 each include genes consisting of nucleotide sequences having 70% or more, preferably 80% or more, more preferably 90% or more, even more preferably 95% or more, most preferably 99% or more homology or identity with the nucleotide sequences shown in SEQ ID Nos: 1, 3, 5, 7, 9, 11 and 13 and encoding proteins having a clock protein activity, respectively. Further, in the present invention, kaiA gene, kaiB1 gene, kaiB2 gene, kaiB3 gene, kaiC1 gene, kaiC2 gene, and kaiC3 gene each also encompass their homologs and orthologs.

The clock proteins KaiA, KaiB1, KaiB2, KaiB3, KaiC1, KaiC2, and kaiC3 each encompass proteins that are functionally equivalent to the proteins consisting of the amino acid sequences shown in SEQ ID NOs: 2, 4, 6, 8, 10, 12, and 14, respectively. Examples of the proteins that are functionally equivalent to the proteins consisting of the amino acid sequences shown in SEQ ID NOs: 2, 4, 6, 8, 10, 12, and 14 each include proteins consisting of amino acid sequences having 70% or more, preferably 80% or more, more preferably 90% or more, even more preferably 95% or more, most preferably 99% or more homology or identity with the amino acid sequences shown in SEQ ID Nos: 2, 4, 6, 8, 10, 12, and 14 and having a clock protein activity, respectively. Further, proteins consisting of amino acid sequences resulting from deletion, substitution, insertion, or addition of one or several amino acids occurring in the amino acid sequences shown in SEQ ID Nos: 2, 4, 6, 8, 10, 12 and 14 and having a clock protein activity are also encompassed. The number of amino acids that are deleted, substituted, inserted, or added is normally 2 to 10, preferably 2 to 5, more preferably 2 or 3.

In the present specification, kaiA gene, kaiB1 gene, kaiB2 gene, kaiB3 gene, kaiC1 gene, kaiC2 gene, and kaiC3 gene may collectively be called kaiABC genes, and KaiA, KaiB1, KaiB2, KaiB3, KaiC1, KaiC2, and kaiC3 may collectively be called KaiABC.

The nucleotide sequences of the genes of interest, including kaiABC genes, can be searched for in a public database (GenBank, EMBL, and DDBJ). For example, among the aforementioned blue-green algae-derived kaiABC genes, blue-green algae-derived kaiABC genes whose sequences are unknown can be obtained by performing cloning using the information of blue-green algae-derived kaiABC genes whose sequences are known. A method for obtaining desired gene by cloning is well known in the field of molecular biology. For example, when gene sequence is known, a suitable genome library is prepared by restriction endonuclease digestion, and then screening can be performed by using a probe complementary to the sequence of the desired gene. Once the sequence is isolated, DNA can be amplified by a standard amplification method such as polymerase chain reaction (PCR) to obtain an amount of DNA suitable for transformation (gene introduction). Methods for producing genome libraries used for cloning of genes, hybridization, PCR, preparing plasmid DNA, cleaving and linking DNA, transformation, and the like are described in, for example, Molecular Cloning: A Laboratory Manual, third edition (Sambrook & Russell, Cold Spring Harbor Laboratory Press, 2001).

Examples of the known sequence IDs of kaiA gene include: slr0756, cce_0424, PCC8801_4233, MAE31730, PCC7424_0601, SYNPCC7002_A0289, Cyan7425_0346, AM1_0994, tlr0481, NIES39_L01230, Synpcc7942_1218, syc0332_d, CYB_0490, CYA_1902, sync_2222, SynRCC307_1826, SYNW0548, Syncc9902_0547, and SynWH7803_1966.

Examples of the known sequence IDs of kaiB1 gene include: slr0757, MAE31740, PCC7424_0600, PCC8801_4232, cce_0423, Tery_3804, Ava_1017, alr2885, NIES39_L01220, Cyan7425_0347, tlr0482, Npun_R2887, AM1_0993, P9303_05431, SynWH7803_1965, Syncc9605_2125, Syncc9902_0548, SYNW0549, PMT1419, and sync_2221.

Examples of the known sequence IDs of kaiB2 gene include: sll1596, RPA0008, MAE31740, sll0486, MAE42960, PCC7424_3005, cce_0423, PCC7424_0600, PCC8801_4232, P9515_15041, CYA_1901, CYB_0489, Tery_3804, P9301_15291, PMM1343, P9215_15721, NIES39_L01220, Ava_1017, alr2885, and slr0757.

Examples of the known sequence IDs of kaiB3 gene include: sll0486, cce_4715, PCC8801_3933, PCC7424_3005, MAE42960, sll1596, Pro1423, CYA_1901, CYB_0489, tlr0482, MAE31740, P9515_15041, PMM1343, PMT9312_1441, P9211_13971, cce_0423, SynRCC307_1825, PCC7424_0600, PCC8801_4232, and P9215_15721.

Examples of the known sequence IDs of kaiC1 gene include: slr0758, PCC8801_4231, PCC7424_0599, cce_0422, MAE31750, SYNPCC7002_A0287, Ava_1016, alr2886, Tery_3805, Npun_R2886, Cyan7425_0348, AM1_0992, tlr0483, syc0334_d, Synpcc7942_1216, NIES39_L01210, CYB_0488, CYA_1900, SynRCC307_1824, and Syncc9902_0549.

Examples of the known sequence IDs of kaiC2 gene include: sll1595, RPA0009, CYB_0488, CYA_1900, tlr0483, AM1_0992, syc0334_d, Synpcc7942_1216, P9211_13961, Syncc9605_2124, MAE31750, SynWH7803_1964, SynRCC307_1824, P9303_05441, sync_2220, PMT1418, NATL1_17691, P9215_15711, SYNW0550, and Pro1423.

Examples of the known sequence IDs of kaiC3 gene include: slr1942, PCC7424_3006, PCC8801_3934, MAE39130, cce_4716, Tery_3805, Cyan7425_0348, tlr0483, syc0334_d, Synpcc7942_1216, AM1_0992, CYA_1900, PCC8801_4231, SYNPCC7002_A0287, slr0758, alr2886, CYB_0488, Ava_1016, MAE31750, and PCC7424_0599.

Examples of a method for overexpressing a clock protein gene in blue-green algae include a method for causing such a mutation that results in the overexpression of a clock protein gene. The overexpression of a clock protein gene in blue-green algae can be achieved by methods known in the art without any particular limitation. Specific examples of a method for overexpressing clock protein gene include a method of introducing a clock protein gene, a method of exchanging a promoter of clock protein gene for such a promoter that causes overexpression of the gene, and a method employing mutation inductions. In the present invention, clock protein genes encompass kaiA gene, kaiB1 gene, kaiB2 gene, kaiB3 gene, kaiC1 gene, kaiC2 gene, and kaiC3 gene as well as kaiABC operon. Overexpression of clock protein gene encompasses overexpression of one or more (two, three, four, five, six, or seven) of kaiA gene, kaiB1 gene, kaiB2 gene, kaiB3 gene, kaiC1 gene, kaiC2 gene, and kaiC3 gene.

Gene introduction can be performed by linking a clock protein gene or a part of a gene to a suitable vector and then introducing the recombinant vector thus obtained into the host blue-green algae in such a manner that the clock protein gene can be expressed, or inserting the clock protein gene or a part of the gene into an arbitrary site in the genome by homologous recombination. The term "a part" indicates a part of clock protein gene that is capable of expressing a protein, which clock protein gene encodes, when the gene is introduced into the host. The clock protein gene to be introduced may be a gene that is derived from a different genus or species from the host blue-green algae; however, the clock protein gene to be introduced is preferably a gene that is derived from the same genus or species as the host blue-green algae. Exchange of a promoter can be performed by, for example, exchanging the promoter of the clock protein gene in the genome for the promoter of interest by homologous recombination. A method employing mutation inductions can be performed by irradiating the parent strain with UV light or treating the parent strain with mutagenic agents (such as N-methyl-N'-nitro-N-nitrosoguanidine and ethyl methanesulfonate), and then selecting a strain that produces a large amount of polyhydroxyalkanoic acid.

A vector to which a gene is linked for gene introduction is not particularly limited as long as it is replicable in the host cells. Examples of the vector include plasmids, phages, and cosmids. In gene introduction performed by homologous recombination with a gene on a chromosome, use of plasmids is not required and a liner gene sequence synthesized by PCR or the like that contains the clock protein gene sequence and the gene sequence of the homologous recombination site at the both ends of sequence can be used. The above liner gene contains, at both ends of its sequence, sequences that are homologous to the gene in the host genome, and the linear gene is introduced into the host chromosome via the homologous sequence.

In the aforementioned vector, a suitable promoter can be linked to the upstream of the clock protein gene thus inserted to ensure that the gene is expressed. The promoter to be used is not limited as long as it is a promoter that allows the expression of the clock protein under nitrogen-deficient conditions in culture using carbon dioxide as the carbon source. The promoter to be used may be appropriately selected by those skilled in the art according to the host. Examples of the promoter include: a promoter of a gene encoding the photosystem II reaction center protein such as a promoter of psbAII; a promoter of cpcA, which is a gene encoding the pigment protein phycocyanin; and a promoter of rbcL, which is a gene encoding a subunit of the carbon fixation enzyme RuBisCO. Further, a constitutive promoter can also be used. A constitutive promoter refers to a promoter that allows a certain level of the constitutive gene expression irrespective of intracellular or extracellular stimulation of the host cell. Examples of the constitutive promoter include, but are not limited to, the artificially synthesized promoter trc.

In addition to a promoter and the gene of interest, selection markers, ribosome binding sequences (SD sequence), and the like may be linked to the vector, if desired. Also, the gene sequence to be introduced may contain a selection marker. Examples of the selection marker include, but are not limited to, drug resistance markers such as kanamycin, spectinomycin, chloramphenicol, and gentamicin.

A known DNA ligase is used for linking genes. A recombinant vector can be obtained by carrying out ligation reactions under prescribed conditions using, preferably, a commercially available ligation kit such as Ligation high (TOYOBO CO., LTD.) and DNA Ligation Kit (TAKARA BIO INC.). Further, if needed, the vectors thus obtained can be purified by the boiling method, the alkaline SDS method, the magnetic bead method, a commercially available kit that is based on the principles of the aforementioned methods, and the like, and further, concentrated by a concentration device such as ethanol precipitation and polyethylene glycol precipitation.

Although gene introduction can be performed by bringing blue-green algae in contact with the vectors or DNA fragments (natural transformation), it is also possible to use the joining method, electroporation, and the like.

A method for inserting the gene of interest into an arbitrary site in the genome by homologous recombination can be carried out by inserting the gene of interest and a promoter into a sequence that is homologous to the genomic sequence, and then introducing the resulting DNA fragment into a cell and causing homologous recombination. When introducing a gene into the genome, a strain in which homologous recombination has occurred can be easily selected by introducing a DNA fragment in which the gene of interest is linked to a selectable marker gene. Further, it is also possible to insert a gene in which a drug resistance gene is linked to a gene that becomes lethal under specific conditions into the genome by homologous recombination according to the aforementioned methods, and then introduce the gene of interest by replacing the drug resistance gene and the gene that becomes lethal under specific conditions with the gene of interest by homologous recombination.

Organic acids, preferably polyhydroxyalkanoic acid, succinic acid, lactic acid, or acetic acid can be produced by culturing the blue-green algae overexpressing clock protein gene obtained as above (for example, transformants of blue-green algae and mutants of blue-green algae) preferably under nitrogen-deficient conditions. When blue-green algae photosynthesize using light energy and carbon dioxide, they can be cultured using carbon dioxide as the carbon source.

Polyhydroxyalkanoic acid (PHA) is a polyester known to be accumulated in a body of certain kind of microorganism, and can be represented by the following chemical formula:

[Formula 1]

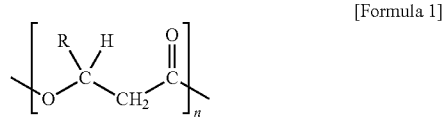

wherein, R may be the same or different and represents a linear or branched alkyl group having 1 to 14 carbon atoms, and n is an integer of 2 or more, preferably an integer of 100 or more, and preferably an integer of 100000 or less.

As PHA is degraded in the natural environment, PHA is expected to be applied to biodegradable plastics and biocompatible materials. Specific examples of PHA include those that are represented by the following chemical formulas.

[Formula 2]

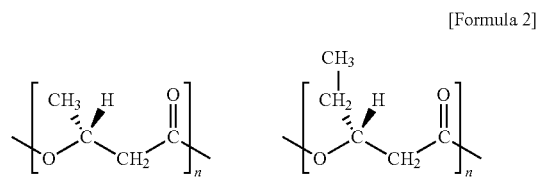

Poly-3-hydroxybutyrate, PHB          Poly-3-hydroxyvalerate, PHV)

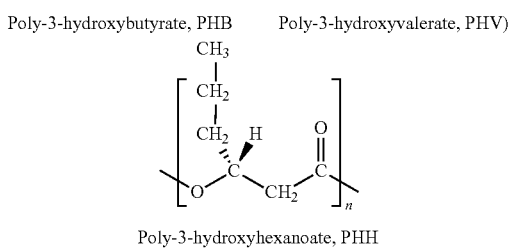

Poly-3-hydroxyhexanoate, PHH

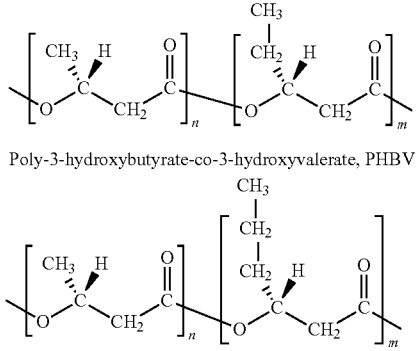

Poly-3-hydroxybutyrate-co-3-hydroxyvalerate, PHBV

Poly-3-hydroxybutyrate-co-3-hydroxyhexanoate, PHBH

Among PHAs, polyhydroxybutyric acid (may also be expresses as PHB and P(3HB)) is known as a biopolymer produced by microorganisms. As a microbially degradable thermoplastic resin, it is expected to serve as a material that can be applied to a wide range of fields such as pharmaceuticals, agricultural chemicals, medical materials, and industrial materials. Polyhydroxybutyric acid (PHB) is a polyester synthesized from acetyl-CoA via three-step reactions. Also, succinic acid and lactic acid are known as raw materials of plastics.

Examples of blue-green algae having the ability to produce polyhydroxybutyric acid include blue-green algae belonging to genus *Synechocystis* such as *Synechocystis* sp. PCC 6803, blue-green algae belonging to genus *Synechococcus* such as *Synechococcus* sp. strain MA19, and blue-green algae belonging to genus *Nostoc* such as *Nostoc muscorum*.

Examples of blue-green algae having the ability to produce succinic acid include blue-green algae belonging to genus *Synechocystis* such as *Synechocystis* sp. PCC 6803, blue-green algae belonging to genus *Microcystis* such as *Microcystis aeruginosa*, blue-green algae belonging to genus *Arthrospira* such as *Arthrospira platensis*, blue-green algae belonging to genus *Cyanothece*, blue-green algae belonging to genus *Anabaena*, blue-green algae belonging to genus *Synechococcus*, blue-green algae belonging to genus *Thermosynechococcus* such as *Thermosynechococcus elongats*, blue-green algae belonging to genus *Gloeobacter* such as *Gloeobacter violaceus*, blue-green algae belonging to genus *Acaryochloris* such as *Acaryochloris marina*, blue-green algae belonging to genus *Nostoc* such as *Nostoc punctiforme*, blue-green algae belonging to genus *Trichodesmium*, blue-green algae belonging to genus *Prochloron*, and blue-green algae belonging to genus *Prochlorococcus*.

Examples of blue-green algae having the ability to produce lactic acid include at least blue-green algae belonging to genus *Synechocystis* such as *Synechocystis* sp. PCC 6803, blue-green algae belonging to genus *Microcystis* such as *Microcystis aeruginosa*, blue-green algae belonging to genus *Arthrospira* such as *Arthrospira platensis*, blue-green algae belonging to genus *Cyanothece*, blue-green algae belonging to genus *Anabaena*, blue-green algae belonging to genus *Synechococcus*, blue-green algae belonging to genus *Thermosynechococcus* such as *Thermosynechococcus elongats*, blue-green algae belonging to genus *Gloeobacter* such as *Gloeobacter violaceus*, blue-green algae belonging to genus *Acaryochloris* such as *Acaryochloris* marina, blue-green algae belonging to genus *Nostoc* such as *Nostoc punctiforme*, blue-green algae belonging to genus *Trichodesmium*, blue-green algae belonging to genus *Prochloron*, and blue-green algae belonging to genus *Prochlorococcus*.

Examples of blue-green algae having the ability to produce acetic acid include at least blue-green algae belonging to genus *Synechocystis* such as *Synechocystis* sp. PCC 6803, blue-green algae belonging to genus *Microcystis* such as *Microcystis aeruginosa*, blue-green algae belonging to genus *Arthrospira* such as *Arthrospira platensis*, blue-green algae belonging to genus *Cyanothece*, blue-green algae belonging to genus *Anabaena*, blue-green algae belonging to genus *Synechococcus*, blue-green algae belonging to genus *Thermosynechococcus* such as *Thermosynechococcus elongats*, blue-green algae belonging to genus *Gloeobacter* such as *Gloeobacter violaceus*, blue-green algae belonging to genus *Acaryochloris* such as *Acaryochloris marina*, blue-green algae belonging to genus *Nostoc* such as *Nostoc punctiforme*, blue-green algae belonging to genus *Trichodesmium*, blue-green algae belonging to genus *Prochloron*, and blue-green algae belonging to genus *Prochlorococcus*.

Although the culture method of the blue-green algae of the present invention is not particularly limited, they are preferably cultured under nitrogen-deficient conditions using carbon dioxide as the carbon source. Under aerobic conditions, the carbon dioxide concentration can be increased by mixing carbon dioxide with air, and the carbon dioxide concentration is preferably adjusted to 0.01 to 10%. Although those skilled in the art can appropriately select suitable media for culture, for example, BG-11 media, MDM media, AO media, ATCC media, CRBIP media, and SP media can be used. Generally, the culture temperature is 20 to 60° C., preferably 25 to 55° C., and the pH of the culture solution is 6 to 12, preferably 7 to 10. The culture time is 4 to 168 hours, preferably 8 to 48 hours.

When polyhydroxyalkanoic acid is produced as the organic acid, preferably blue-green algae overexpressing kaiB gene or kaiC gene are cultured. The blue-green algae overexpressing kaiB gene or kaiC gene encompass blue-green algae overexpressing only kaiB gene, blue-green algae overexpressing only kaiC gene, and blue-green algae overexpressing kaiB gene and kaiC gene. Particularly preferably, blue-green algae overexpressing kaiB3 gene and blue-green algae overexpressing kaiC3 gene are cultured. These blue-green algae are cultured in media such as the aforementioned BG-11 media under light irradiation and aerobic conditions (light aerobic condition). The light intensity is preferably 20 to 150 micromole photons (per second and square meter). Also, the culture may be carried out under light irradiation, and then switched to under shielded light (light-dark condition). In order to increase the percentage of PHA accumulation in the bacterial body, it is preferable to culture the isolated bacterial bodies of blue-green algae under nitrogen-deficient conditions, for example, in a culture solution having a limited nitrogen source, for example, BG-11 media from which sodium nitrate is removed. As shown above, PHA is produced and accumulated in the bacterial bodies of blue-green algae, and the resulting PHA is collected from the culture product.

When succinic acid is produced as the organic acid, preferably blue-green algae overexpressing kaiB gene or kaiC gene are cultured. Particularly preferably, blue-green algae overexpressing kaiB3 gene and blue-green algae overexpressing kaiC3 gene are cultured. By culturing these blue-green algae in media such as the aforementioned BG-11 media under light aerobic conditions, and then blocking light and setting conditions in which oxygen is substantially absent (dark anaerobic condition), which are created by, for example, replacing the air with nitrogen gas, succinic acid is excreted out of the cells and then the succinic acid is collected from the culture product. Since succinic acid is excreted out of the cells, purification of the acid can be carried out at low cost. Conditions in which oxygen is substantially absent refer to conditions in which the concentration of oxygen is, for example, 1% or less, preferably 0.5% or less, more preferably 0.2% or less.

When lactic acid is produced as the organic acid, preferably blue-green algae overexpressing kaiB gene or kaiC gene are cultured. Particularly preferably, blue-green algae overexpressing kaiB1 gene, blue-green algae overexpressing kaiB2 gene, blue-green algae overexpressing kaiB3 gene, blue-green algae overexpressing kaiC1 gene, blue-green algae overexpressing kaiC2 gene, and blue-green algae overexpressing kaiC3 gene are cultured. BY culturing these blue-green algae in media such as the aforementioned BG-11 media under light aerobic conditions, and then setting dark anaerobic conditions, lactic acid is excreted out of the cells and then the lactic acid is collected from the culture product. Since lactic acid is excreted out of the cells, purification of the acid can be carried out at low cost.

When acetic acid is produced as the organic acid, preferably blue-green algae overexpressing kaiB gene or kaiC gene are cultured. Particularly preferably, blue-green algae overexpressing kaiB2 gene, blue-green algae overexpressing kaiB3 gene, blue-green algae overexpressing kaiC1 gene, blue-green algae overexpressing kaiC2 gene, and blue-green algae overexpressing kaiC3 gene are cultured. By culturing these blue-green algae in media such as the aforementioned BG-11 media under light aerobic conditions, and then setting dark anaerobic conditions, lactic acid is excreted out of the cells and then the acetic acid is collected from the culture product. Since acetic acid is excreted out of the cells, purification of the acid can be carried out at low cost.

The term "culture product" encompasses, for example, in addition to the culture solution containing the cultured blue-green algae, the supernatant of the culture solution, the cultured cells or bacterial bodies, or the disrupted cultured cells or bacterial bodies. When, for example, organic acids are produced within the bacterial bodies or cells, the acids can be isolated by disrupting the bacterial bodies or cells after culture. Also, when, for example, organic acids are produced outside the bacterial bodies or cells, the culture solution can be directly used or the acids can be isolated by removing the bacterial bodies or cells from the culture solution by centrifugation. Thereafter, organic acids can also be purified from the culture product by using one or an appropriate combination of the methods normally employed in the art. Examples of the method of purification include, but are not particularly limited to, a method for extracting the organic acids by dissolving them in an organic solvent in which they are soluble, and a method for obtaining organic acids by removing the components of the bacterial body other than the organic acids by solubilizing them and the like. Examples of the extraction solvent include alcohols such as methanol and ethanol, hexane, acetone and halogenated hydrocarbon such as chloroform and 1,2-dichloroethane. For example, as a method for collecting organic acids from culture product, the method of G. Braunegg et al. (European Journal of Applied Microbiology and Biotechnology 6, 29 to 37 (1978)) and the method of M. Kato et al. (Appl. Microbiol. Biotechnol. 45: 363 to 370 (1996)) can be used.

In the case of a clock protein-overexpressing strain, the amount of PHA produced by the blue-green algae of the present invention per L of culture solution is preferably 1.4 to 2.0 times as much as the wild-type strain. In the case of a clock protein-overexpressing strain, the production amount of succinic acid by the blue-green algae of the present invention per L of culture solution is preferably 1.2 to 2.0 times as much as the wild-type strain. In the case of a clock protein-overexpressing strain, the production amount of lactic acid by the blue-green algae of the present invention per L of culture solution is preferably 1.2 to 2.0 times as much as the wild-type strain. In the case of a clock protein-overexpressing strain, the production amount of acetic acid by the blue-green algae of the present invention per L of culture solution is preferably 1.2 to 2.0 times as much as the wild-type strain.

Accordingly, the present invention enables the efficient production of organic acids, particularly PHA, succinic acid, lactic acid, and acetic acid.

Hereinbelow, the present invention will be more specifically described based on Examples. However, the present invention is not limited to these Examples.

EXAMPLES

Example 1

Construction of Clock Protein Gene-overexpressing Strains

Using *Synechocystis* sp. PCC 6803 (hereinbelow, referred to as *Synechocystis*) cells, which are unicellular cyanobacteria (unicellular blue-green algae), strains overexpressing seven clock protein genes (kaiA, kaiB1, kaiB2, kaiB3, kaiC1, kaiC2, and kaiC3) were constructed. *Synechocystis* sp. PCC 6803 is available from The Pasteur Institute (France) (http://www.pasteur.fr/ip/easysite/pasteur/en/research/collections/crbip/general-informations-concerning-the-collections/iv-the-open-collections/iv-iii-pasteur-culture- collection-of-cyanobacteria).

Specifically, a promoter of psbAII, which encodes the photosystem II reaction center protein, is attached to the ORF of the gene, and the resulting gene was introduced into a region in the genome that would result in less impact. As the vector, pTKP2031V was used (Osanai et al., 2011, J. Biol. Chem. 286; 30962 to 30971). Specifically, the clock protein-overexpressing strains were produced as follows.

Using the genomic DNA of *Synechocystis* as a template, the ORF region of each of the clock proteins kaiA, kaiB1, kaiB2, kaiB3, kaiC1, kaiC2, and kaiC3 was amplified by PCR using KOD polymerase (TOYOBO CO., LTD.) and primers (see Table 1 below). The fragments thus obtained were cleaved at the termini with NdeI and HpaI (TAKARA BIO INC.) and then introduced into the NdeI-HpaI region of pTKP2031V, a vector for *Synechocystis*. For ligation, DNA Ligation kit (TAKARA BIO INC.) was used. The sequences of the plasmids thus completed were confirmed by sequencing.

TABLE 1

| | |
|---|---|
| KaiA-TKPF: | ATTATTCATATGCAGTCTCCCCTCTC (SEQ ID NO: 15) |
| KaiA-TKPRHpa: | AAACCCGTTAACTTAATCCGTCTGATAATA (SEQ ID NO: 16) |
| KaiB1-TKPF: | ATTATTCATATGAGCCCCTTTAAAAAA (SEQ ID NO: 17) |
| KaiB1-TKPRHpa: | AAACCCGTTAACCTATTGGTCTTCTGCTTC (SEQ ID NO: 18) |
| KaiB2-TKPF: | ATTATTCATATGGAAAATTTAAACGCT (SEQ ID NO: 19) |
| KaiB2-TKPRHpa: | AAACCCGTTAACCTAGATTTTCCAATCCAT (SEQ ID NO: 20) |
| KaiB3-TKPF: | ATTATTCATATGGATATGAATAGGATT (SEQ ID NO: 21) |
| KaiB3-TKPRHpa: | AAACCCGTTAACTTAATCCTCCGGCAAACG (SEQ ID NO: 22) |
| KaiC1-TKPF: | ATTATTCATATGAACTTACCGATTGTT (SEQ ID NO: 23) |
| KaiC1-TKPREcoRV: | AAAGGGGATATCCTACTCAGCGGTCTTGTC (SEQ ID NO: 24) |

TABLE 1-continued

| | |
|---|---|
| KaiC2-TKPF: | ATTATTCATATGACAGATAACAGCCAA (SEQ ID NO: 25) |
| KaiC2-TKPRHpa: | AAAGGGGTTAACTTAGGGGTTTTGATAAATG (SEQ ID NO: 26) |
| KaiC3-TKPF: | ATTATTCATATGATCGACCAAGAGACA (SEQ ID NO: 27) |
| KaiC3-TKPRHpa: | AAAGGGGTTAACCTATATTTTCTCATCGAA (SEQ ID NO: 28) |

Transformation of *Synechocystis* was carried out as follows. To 200 μl of culture solutions containing the wild-type strain of *Synechocystis* (GT strain) at a concentration of $A_{730}$=2 to 3, about 100 ng of pTKP2031V-hik8 was added, and the bacteria were spread on the mixed cellulose membrane (MERCK MILLIPORE CORPORATION) placed on BG-11 plates. After culturing the bacteria in an incubator for cyanobacteria for one day, the membranes were transferred to BG-11 plates containing 50 μg/ml kanamycin, followed by about three weeks of culture. The colonies thus obtained were passaged three times on BG-11 plates containing the same concentration of kanamycin, whereby strains overexpressing each of the aforementioned clock proteins were established. The composition of the BG-11 medium is as follows.

TABLE 2

| <BG-11 medium composition> | |
|---|---|
| NaNO$_3$ | 1.5 g (17.65 mM) |
| K$_2$HPO$_4$ | 0.03 g (0.18 mM) |
| MgSO$_4$•7H$_2$O | 0.075 g (0.30 mM) |
| CaCl$_2$•2H$_2$O | 0.036 g (0.25 mM) |
| Citric acid | 0.006 g (0.03 mM) |
| Ammonium ferric citrate | 0.006 g (0.03 mM) |
| EDTA | 0.001 g (0.003 mM) |
| Na$_2$CO$_3$ | 0.02 g (0.19 mM) |
| HEPES-KOH(pH 8.0) | 4.77 g (20 mM) |
| Trace metal mixture A5 + Co | 1 ml |
| H$_2$O | Up to 1 L |
| <Trace metal mixture A5 + Co> | |
| H$_3$BO$_3$ | 2.86 g |
| MnCl$_2$•4H$_2$O | 1.81 g |
| ZnSO$_4$•7H$_2$O | 0.222 g |
| Na$_2$MoO$_4$•2H$_2$O | 0.390 g |
| CuSO$_4$•5H$_2$O | 0.079 g |
| Co(NO$_3$)$_2$•6H$_2$O | 0.049 g |
| H$_2$O | Up to 1 L |

Hereinafter, in BG-11 liquid media, 17.65 mM NaNO$_3$ was removed and 3 mM NH$_4$Cl was used as a nitrogen source. Nitrogen-deficient conditions were created by allowing the ammonia source to be completely consumed or resuspending cells collected by filters in media from which the nitrogen source had been removed.

With respect to each of the clock protein-overexpressing strains obtained and the parent strain (GT), the amount of mRNA of each clock protein was measured by real-time PCR. In each of the clock protein-overexpressing strains, the amount of mRNA of each clock protein was increased compared to the parent strain.

Example 2

Measurement of the Amount of Polyhydroxybutyric Acid (PHB) Produced

The amount of intracellular accumulation of polyhydroxybutyric acid (PHB) was measured with respect to each of the clock protein-overexpressing strains (kaiAox, kaiB1ox, kaiB2ox, kaiB3ox, kaiC1ox, kaiC2ox, kaiC3ox) produced in Example 1 and the wild strain (GT).

In this example, 3 mM ammonium chloride was added to the media lacking the nitrogen source (BG-110) as the initial nitrogen source, which was then allowed to be completely consumed, whereby nitrogen-deficient conditions were created. All the cultures were performed under aerobic light conditions at 30° C. The light intensity was set at 50 to 80 micromole photons/m$^2$s. Also, in aerobic culture, air mixed with 1% CO$_2$ was introduced into the culture solutions. After nine days of culture, cells were collected by centrifugation. The collected cells were freeze-dried at −80° C. for three days, and then suspended in chloroform, and incubated for four days at 70° C., followed by five minutes of sonication. The process was performed eight times in total. The resulting disruption solutions were filtered, followed by extraction and purification using hexane, chloroform, methanol, and the like. The weight of the samples thus obtained was determined as the amount of PHB.

It was found that the amount of PHB per L of culture solution was about 7 mg for the wild-type strain (GT), whereas that was increased to about 14 mg and about 10 mg for kaiB3-overexpressing strain and kaiC3-overexpressing strain (i.e., kaiB3ox and kaiC3ox), respectively.

Example 3

Measurement of the Production Amount of Succinic Acid, Lactic Acid, and Acetic Acid The production amount of succinic acid, lactic acid, and acetic acid was measured in each of the clock protein-overexpressing strains produced in Example 1 (kaiAox, kaiB1ox, kaiB2ox, kaiB3ox, kaiC1ox, kaiC2ox, and kaiC3ox) and the wild-type strain (GT).

With respect to organic acids such as succinic acid, lactic acid, and acetic acid, the amount in culture solutions obtained under anaerobic dark conditions was measured. Firstly, each of the blue-green algae strains was cultured in 70 ml of normal media under aerobic light conditions at 30° C. In aerobic culture, air mixed with 1% CO$_2$ was introduced into the culture solutions. After three days of culture, cells were concentrated and suspended in 10 ml of a 20 mM Hepes-KOH (pH 7.8) solution so that the turbidity $A_{730}$=20, and transferred to vials for gas chromatography. The vials were plugged with butyl-rubber caps, which were pieced with two injection needles, through one of which nitrogen gas was introduced for one hour. Thereafter, the injection needles were removed, whereby the anaerobic conditions were created in the vials. Subsequently, the vials were wrapped with aluminum foil to create dark conditions, followed by shaking at 30° C. for three days. The culture solutions were then centrifuged to separate cells, and the supernatants were transferred to new tubes and then freeze-dried to solidify the contents. The solidified products were then suspended in perchloric acid and analyzed by high performance liquid chromatography (HPLC). Quantification was performed by the post-labeling method using bromothymol blue.

Measurement 1:

The production amount of succinic acid, lactic acid, and acetic acid by the wild-type strain per L of culture solution was about 20 mg, 275 mg, and 16 mg, respectively. It was found that the production amount of succinic acid per L of culture solution increased to 25 mg and 30 mg by overexpressing kaiB3 and kaiC3, respectively. The production amount of lactic acid increased to 546 mg, 447 mg, and 408 mg by overexpressing kaiB1, kaiB2, and kaiC1, respectively. Also, the production amount of acetic acid per L of culture solution increased to 21 mg by overexpressing kaiB3, respectively.

Measurement 2:

The production amount of succinic acid, lactic acid, and acetic acid by the wild-type strain per L of culture solution was about 13 mg, 5 mg or less, and 167 mg, respectively. It was found that the production amount of succinic acid per L of culture solution increased to 19 mg and 26 mg by overexpressing kaiB3 and kaiC3, respectively. The production amount of lactic acid increased to 16 mg, 10 mg, and 12 mg by overexpressing kaiB1, kaiB2, and kaiC1, respectively. Also, the production amount of acetic acid per L of culture solution increased to 266 mg and 279 mg by overexpressing kaiB3 and kaiC3, respectively.

All references, including any publications, patents or patent applications cited in this specification are hereby incorporated by reference in their entirely.

The invention claimed is:

1. Blue-green algae transformed by overexpressing clock protein genes, wherein the clock protein genes are kaiB gene and kaiC gene.

2. The blue-green algae according to claim 1, wherein the blue-green algae has an ability to produce polyhydroxyalkanoic acid.

3. The blue-green algae according to claim 1, wherein the blue-green algae has phaAB gene and phaEC gene.

4. The blue-green algae according to claim 1, wherein the blue-green algae belongs to genus *Synechocystis*.

5. A method for producing an organic acid, comprising culturing the blue-green algae of claim 1, and collecting an organic acid.

6. The method according to claim 5, wherein the organic acid is polyhydroxyalkanoic acid, and the blue-green algae has an ability to produce polyhydroxyalkanoic acid.

7. The method according to claim 6, wherein the blue-green algae has phaAB gene and phaEC gene.

8. The method according to claim 6, wherein the polyhydroxyalkanoic acid is polyhydroxybutyric acid.

9. The method according to claim 5, wherein the organic acid is succinic acid or lactic acid.

10. The method according to claim 5, wherein the blue-green algae belongs to genus *Synechocystis*.

11. The method according to claim 5, wherein the culture is performed under nitrogen-deficient conditions.

12. A method for enhancing an ability to produce an organic acid in blue-green algae, comprising overexpressing the clock protein genes of claim 1 in the blue-green algae, wherein the organic acid is polyhroxyalkanoic acid, and the blue-algae has phaAB gene and phaEC gene.

13. The method according to claim 12, wherein the polyhydroxyalkanoic acid is polyhydroxybutyric acid.

14. The method according to claim 12, wherein the blue-green algae belongs to genus *Synechocystis*.

15. The method according to claim 12, wherein the blue-green algae is cultured under nitrogen-deficient conditions.

* * * * *